United States Patent [19]
Desjardins et al.

[11] Patent Number: 6,156,208
[45] Date of Patent: Dec. 5, 2000

[54] FERROGRAPHIC METHOD

[75] Inventors: John B. Desjardins, Leominster; William W. Seifert, Wellesley Hills; Robert S. Wenstrup, Wayland; Vernon C. Westcott, Lincoln, all of Mass.

[73] Assignee: Institute Guilfoyle, Belmont, Mass.

[21] Appl. No.: 09/082,067

[22] Filed: May 20, 1998

[51] Int. Cl.$^7$ .............................. B01D 35/06; G01N 21/05
[52] U.S. Cl. ..................... 210/695; 210/222; 209/214; 356/38; 356/246
[58] Field of Search .................................. 210/695, 222; 209/214; 356/246, 38

[56] References Cited

U.S. PATENT DOCUMENTS

| | | | |
|---|---|---|---|
| 3,647,304 | 3/1972 | Emmel et al. | 356/246 |
| 4,047,814 | 9/1977 | Westcott | 209/214 |
| 5,393,494 | 2/1995 | Greenfield et al. | 422/68.1 |
| 5,552,885 | 9/1996 | Steen | 356/246 |
| 5,714,059 | 2/1998 | Seifert et al. | 210/222 |

FOREIGN PATENT DOCUMENTS 0 672 458 A2  9/1995  European Pat. Off. .

*Primary Examiner*—David A. Reifsnyder
*Attorney, Agent, or Firm*—Cesari and McKenna, LLP

[57] ABSTRACT

A ferrographic apparatus and method incorporate a priming operation that moves a priming fluid, in a direction opposite to the flow direction subsequently followed by the sample fluid, through a fluid pathway including the flow chamber. The fluid pathway is configured to facilitate dissipation of any gas bubble introduced into it during the priming operation and to reduce adventitious deposition of specimen material at locations other than the substrate. Sample fluid to be analyzed is added to the reservoir so as to form a bubble-free interface with the priming fluid, and the direction of movement through the flow chamber is reversed. The resulting continuous fluid column is advanced through the fluid pathway so that the sample fluid enters the flow chamber through the inlet port and passes through the magnetic field gradient, exiting through an orifice at the opposite end of the flow chamber serving as the outlet port. The flow chamber of the ferrograph is preferably contained in a deposition cassette comprising the substrate, a gasket and a platen which incorporates an integral fluid reservoir in communication with the inlet port. A pump is preferably configured to move each liquid through the fluid pathway at a distinct flow rate and in a direction according to the function performed by the respective liquid.

22 Claims, 4 Drawing Sheets

FERROGRAPHIC METHOD

BACKGROUND OF THE INVENTION

Ferrography is a method of separating suspended particles displaying magnetic properties from a liquid by passing the liquid through a magnetic field. The interaction between the magnetic field through which the particles move and the magnetic dipole moments of the particles causes the particles to deposit onto a substrate in the region of strongest field gradient. This approach, applied to removing wear particles from used lubricating oil, was first described in U.S. Pat. No. 4,047,814, herein incorporated by reference.

Ferrographic techniques have also been applied to cell sorting methods that exploit differences in surface protein compositions of biological cells, such as find wide application in research and in diagnostic procedures relating to cancer and immunodeficiency diseases, as well as in other biomedical applications. This type of analysis is based on the ability of magnetic tags conjugated to appropriate antibodies to attach to specific surface protein compositions. For example, after magnetic tagging, lymphocytes may be readily sorted ferrographically. This approach to cell sorting efficiently concentrates the cells of interest and thus does not require sophisticated fluidic or optical systems for subsequent study or counting of the cells.

U.S. Pat. No. 5,714,059, herein incorporated by reference, discloses an analytical ferrograph, also called an analytical magnetic cytometer, suitable for magnetically driven cell deposition. Its magnet has pole members defining an interpolar gap therebetween with a relatively high magnetic flux density. For ferrographic analysis of biological cells suspended in a sample fluid, an aliquot of the sample fluid is passed through a liquid-tight flow pathway, including a flow chamber which is part of a larger flow unit, disposed in the fringing magnetic field. In the flow chamber, this flow pathway is defined by opposing parallel plates, one of which, the substrate, is mounted against the pole members and over the gap. Particles that are magnetically susceptible (either naturally or due to prior preparation by techniques well known to those skilled in the art) are separated from the balance of the sample fluid, and are deposited onto a deposition surface, i.e., the interior surface of the substrate, facing away from the pole gap. After the entire aliquot has passed through the flow chamber, the flow unit is disassembled and the deposit is analyzed.

A flow chamber in the flow unit is defined by a hole through a spacer sheet, or gasket, of elastomeric material disposed between the two plates, one of which is the substrate and the other of which is referred to herein as the platen. Pressure applied perpendicularly to the substrate surface maintains the integrity of the seal around each flow chamber. Or, electrostatic or frictional forces can hold the plates against the spacer sheet, parallel to one another. Free ends of the sheet extending beyond the edges of the substrate and platen facilitate disassembly of the unit without disruption of the substrate or deposit.

A flow unit including several parallel flow chambers, each defined by a hole through the gasket, is used to permit simultaneous processing of several aliquots under identical flow and magnetic field conditions. Collection of the resulting deposits in compact form on a single deposition surface facilitates comparison of different deposits derived from the same fluid source.

Several features of the flow unit promote optimal performance of such a system. Typically, the substrate onto which the cells are deposited is a thin slide of common borosilicate glass. The optical transparency, mechanical rigidity, smooth surface, and low chemical reactivity of glass facilitate analysis of the deposit after removal of the flow chamber from the apparatus. A very thin substrate—preferably on the order of 100 micrometers—allows the deposition surface to be as close as possible to the interpolar gap so that tagged cells in the fluid flowing adjacent the gap encounter strong field gradients which efficiently draw the cells to the surface, where they are deposited in compact, well-defined regions. Finally, the flow unit is economically disposable after a single use to satisfy hygienic requirements.

Although known ferrographic systems effectively separate biological cells, several characteristics of past fluid pathway implementations have limited their serviceability. For example, to form a fluid pathway, thin tubing is typically joined to the flow unit at two orifices in the platen which serve as ports for a single flow chamber. As the sample fluid passes through such a pathway, surface irregularities—such as discontinuities, crevices or diameter changes—along the length of tubing and especially at the joints, induce suspended material, including magnetically tagged bodies of interest, to be caught and remain at these unintended deposition sites. Specimen matter is lost in greater quantity with an increase in the tubing length or the number and/or abruptness of diameter changes experienced by the sample fluid before it reaches the desired deposition site on the substrate. Processing protocols entailing moving the sample fluid through the flow chamber in one direction and then reversing the flow direction to pass the same fluid through the flow chamber a second time also are predisposed to loss of specimen matter.

Another difficulty with known systems is related to the processing of several fluids. The aliquot of sample fluid is typically followed through the fluid pathway by one or more additional liquids in order to interact with material deposited on the substrate. For example, one such liquid may stain deposited cells to facilitate their visual examination. A rinse fluid may then be applied to remove extraneous stain material or, even if no stain is applied in situ, to reduce the number of nonmagnetic elements entrained in the deposit. Such a multi-fluid sequence is often implemented by consecutively disposing the several liquids in one of the lengths of tubing and then moving the liquids through the flow chamber. Gas bubbles at the interfaces between adjacent fluids collect in the flow chamber, interfering with deposition of specimen material. The total amount of sample fluid that can be conveniently processed is limited by the tubing volume. The surface irregularities and extended distance which the interface between adjacent fluids traverses dispose the fluids to premature and uncontrolled mixing which, in the case of a staining liquid following the sample fluid, impairs control of the staining operation.

DESCRIPTION OF THE INVENTION

Objects of the Invention

It is, accordingly, an object of the invention to provide a ferrographic apparatus and method that allows processing of a sample fluid without introducing bubbles into the fluid pathway.

It is another object of the invention to provide such an apparatus and method capable of processing arbitrarily large sample volumes.

It is yet another object of the invention is to provide such an apparatus and method that reduces the loss of specimen material by unintended deposition of suspended material before it passes through the magnetic field.

It is yet another object of the invention to provide such an apparatus and method capable of capturing cells present in a sample fluid at very low concentrations.

It is yet another object of the invention to provide such an apparatus and method capable of consecutively processing several fluids without introducing gas bubbles into the fluid pathway, and with minimal mixing therebetween.

Yet another object of the invention is to provide such an apparatus and method that affords improved exposure control of specimen material displaying magnetic properties to staining agents.

Another object of the invention is to provide such an apparatus and method that minimizes subjection of the specimen materials to destructive conditions, such as passage through a peristaltic pump, before they pass through the flow chamber.

It is another object of the invention to provide such an apparatus and method capable of efficiently removing extraneous material from the deposit.

Brief Summary of the Invention

The invention provides a ferrographic apparatus and method that enable the production of deposits of consistent quality by an uncomplicated specimen handling procedure. The system of the invention incorporates a priming operation that moves a priming fluid, in a direction opposite to the flow direction subsequently followed by the is sample fluid, through a fluid pathway including the flow chamber. The fluid pathway is configured to facilitate dissipation of any gas bubble introduced into it during the priming operation and to reduce adventitious deposition of specimen material at locations other than the substrate.

In one aspect, the method of the invention incorporates a priming operation that moves a priming fluid slowly into the flow chamber until its meniscus has left the flow chamber through an orifice in the platen serving as an inlet port at one end of the flow chamber. Any gas bubble traveling with the priming fluid meniscus is displaced through the inlet port into a reservoir. The reservoir is preferably of sufficient diameter to allow any bubble at the liquid surface to readily burst. The sample fluid to be analyzed is then added to the reservoir so as to form a bubble-free interface with the priming fluid, and the direction of movement through the flow chamber is reversed. The resulting continuous fluid column is advanced through the fluid pathway so that the sample fluid enters the flow chamber through the inlet port and passes through the magnetic field gradient, exiting through an orifice at the opposite end of the flow chamber serving as the outlet port.

If additional fluid, such as extra sample fluid or a staining or rinsing solution, is to be passed through the flow chamber, it is added to the reservoir before the sample fluid meniscus has reached the inlet port in order to form a bubble-free interface with the fluid already in the reservoir. Each fluid addition is similarly introduced by placing it into the reservoir so as to form an interface with the liquid preceding it. In one embodiment the reservoir is open to the atmosphere so that additional fluid can be introduced by pipette. In another embodiment, the reservoir is capped and functions as a drip chamber for a larger vessel of fluid. Fluid may be added to the top of the reservoir as it is being drawn into the chamber from the bottom; or, the fluid column may be static during fluid additions. In any of these cases, the capacity to continually add fluid to the reservoir allows arbitrarily large fluid volumes, much greater than the reservoir volume to be processed.

In another aspect, the flow chamber of the ferrograph of the invention is contained in a deposition cassette comprising the substrate, a gasket and a platen which incorporates an integral fluid reservoir in communication with the inlet port. Including the reservoir in the deposition cassette eliminates surface discontinuities present at an inlet port-tubing joint and reduces the length of the fluid pathway traversed by the sample fluid. Both of these attributes minimize opportunity for adventitious deposition, which affords the invention a greater capture efficiency and suits the cassette for the analysis of cells present at very low concentrations. The integral reservoir and short pre-flow chamber promote the preservation of a relatively sharp interface between different consecutive liquids; such an interface remains substantially intact during movement through the fluid pathway, with any mixing across the interface occurring over an insignificant distance compared to the total length in the fluid column of the fluids forming the interface, so that the exposure of the matter in one of the liquid to matter in the other of the liquids does not occur in an uncontrolled fashion. The reservoir is preferably tapered to broaden away from the inlet port so that a diameter sufficient for bubble dissipation is realized without any abrupt diameter changes. The deposition cassette of the invention is compact and convenient for the user; once the assembled cassette is loaded into the ferrograph, no further connections to the inlet port are necessary in order to add fluid to the reservoir.

These two aspects are especially advantageous in combination in that they permit the serial processing of several fluids without the introduction of bubbles or significant mixing therebetween. The invention achieves this functionality without a complex system of valves for feeding distinct liquids into the system.

An outlet conduit in communication with the outlet port receives fluid leaving the flow chamber. A pump operating on the outlet conduit controls the movement of fluid through the fluid pathway. The location of the outlet port-conduit joint and of the pump downstream from the deposition chamber protects the specimen cells respectively from unintended deposition sites and from potentially destructive mechanical action before exposure to the magnetic field.

In another aspect of the invention, the pump is configured to move each liquid through the fluid pathway at a distinct flow rate and in a direction according to the function performed by the respective liquid. For example, the pump may force priming fluid into the reservoir at a moderate priming rate, then reverse direction to draw sample fluid through the flow chamber at a slower sample fluid rate, and finally use a much greater rate, for example 10, 20, 50 or 100 times the sample fluid rate, for rinsing. The sample fluid rate is chosen to allow the specimen material sufficient residence time in the flow chamber to be deposited on the substrate; a high rinsing rate provides force adequate to efficiently remove entrained nonmagnetic material while the specimen material of interest is held securely on the substrate by the magnetic field. A staining solution following the sample fluid may be moved along the fluid pathway at zero velocity—that is, allowed to remain stationary in the flow chamber—for a fixed length of time in order to regulate the interaction between the deposit and the staining agent.

In one embodiment, the deposition cassette is removed from the ferrograph before rinsing so that, free from the restraining force of the magnetic field, the deposit is flushed off the substrate and out of the chamber. Such a flushing step may be preceded by a rinse fluid containing an enzymatic agent that acts to alter the bond between the deposited material and the substrate so as to facilitate removal of the deposit by flushing. Any of the staining, rinsing, or flushing steps may be applied selectively to some or all of the flow chambers of a multi-chambered cassette.

The language of this description is not intended to limit the invention to the treatment of biological cells but rather is directed in general to the separation of suspended magnetic particulate matter from a fluid, be the particulate matter, for example, organic, inorganic, geological, or colloidal in nature. As used herein, the phrase "a material displaying magnetic properties" includes ferromagnetic, paramagnetic, superparamagnetic and diamagnetic materials. Thus, the invention may be used to expose a suspended diamagnetic material to a magnetic field gradient so as to repel it from the substrate, thereby effecting separation of the diamagnetic material from other material in the fluid. Also, although the invention is sometimes described herein in terms of a single-flow-chamber deposition cassette, the invention also encompasses flow units accommodating several parallel flow chambers.

BRIEF DESCRIPTION OF THE DRAWINGS

The invention description below refers to the accompanying drawings, in which identical reference numerals refer to the same component, of which.

DETAILED DESCRIPTION OF AN ILLUSTRATIVE EMBODIMENT

Figure 1:
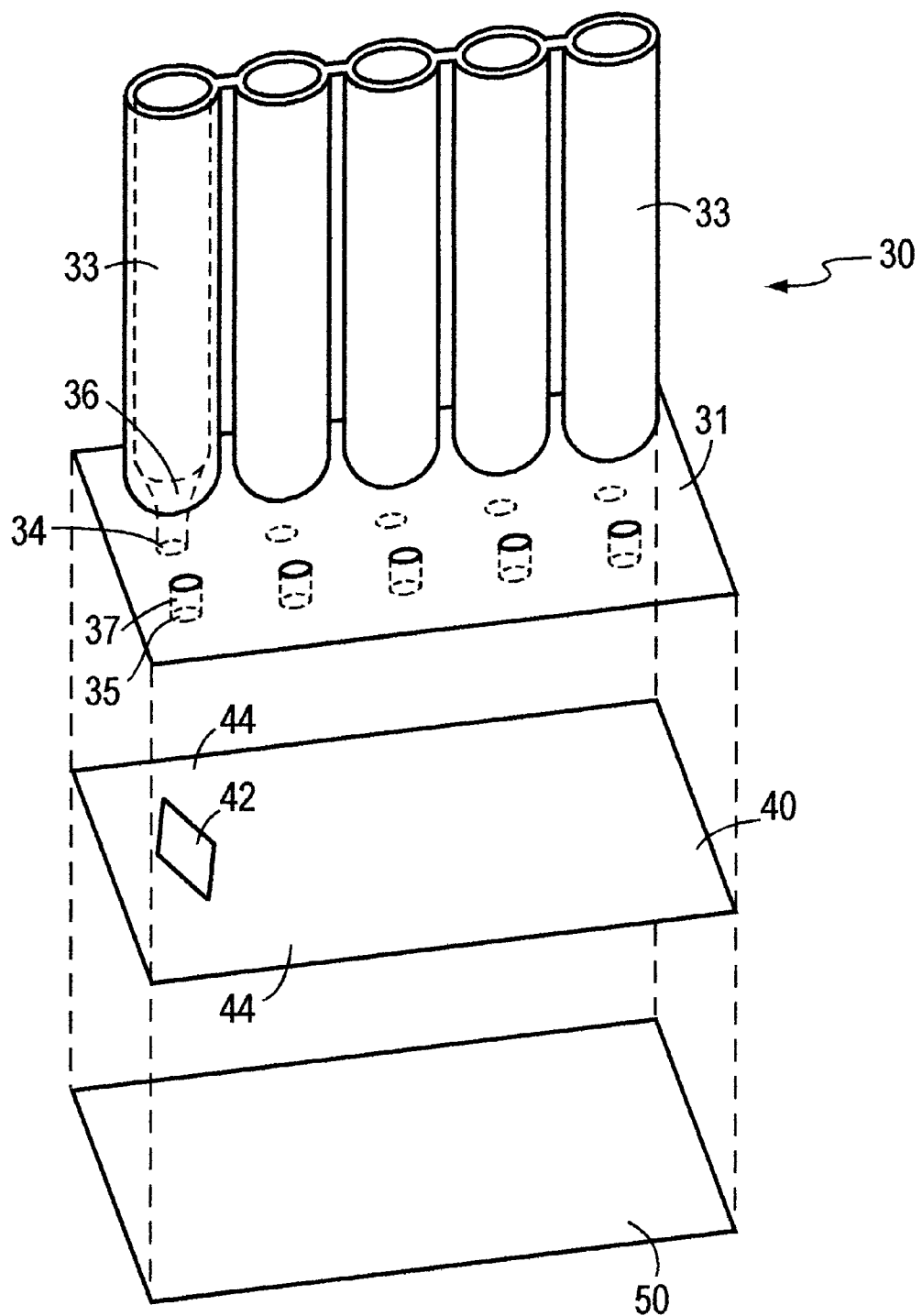
FIG. 1 shows a deposition cassette of the invention in exploded view.

The deposition cassette of the invention comprises a mutually parallel substrate and platen and a thin gasket of elastomeric polymer interposed between them, having features and dimensions as generally described in the '059 patent. FIG. 1 shows the particular features of an illustrative embodiment having five identical parallel flow chambers, the details of only one of which is indicated. The deposition cassette 20 is comprises a platen 30 and a substrate 50 with a gasket 40 interposed therebetween. The platen 30 includes a planar portion 31, which forms a seal against the gasket 40, and a reservoir portion including fluid reservoirs 33. An aperture 34 in the gasket side of the platen and in fluid communication with the reservoir 33 serves as an inlet port for the flow chamber. An outlet port 35 in the gasket side of the platen 40 opens onto an outlet channel 37 at which an outlet conduit, not shown, may be attached. The reservoir 33 preferably includes a tapered section 36 over which the diameter of the reservoir 33 increases from its value at the inlet port 34 to a value sufficiently large to allow ready dissipation of gas bubbles. For most applications, the platen 30 is preferably optically transparent and of a relatively rigid polymeric material.

The gasket 40 is continuous except for one chamber hole 42 therethrough for each flow chamber in the cassette 20. The inlet and outlet ports 34 and 35 extend through the platen 30 over opposite ends of a chamber hole 42 to provide for fluid flow through a flow chamber formed by the hole in the assembled cassette. The gasket 40 is preferably of a material that electrostatically adheres to the platen 30 and the glass substrate 50, thereby forming a conformal coating and self-sealing the periphery of each chamber hole 42 to form a flow chamber upon slightly pressing together the members during assembly of the cassette 20. It is also desirable that the gasket material not be wet by any fluids to be used in the flow chamber. Silicone rubber and latex rubber have proven suitable materials for the gasket 40. The gasket 40 preferably has opposite free ends 44 extending beyond the edges of the platen 30 and substrate 50 to permit easy, nondestructive disassembly of the cassette 20 after use. The geometry of the chamber hole 42 of the invention is not limited to the tapered form shown; other shapes, such as elliptical or oblong, may also be used.

Figure 2:
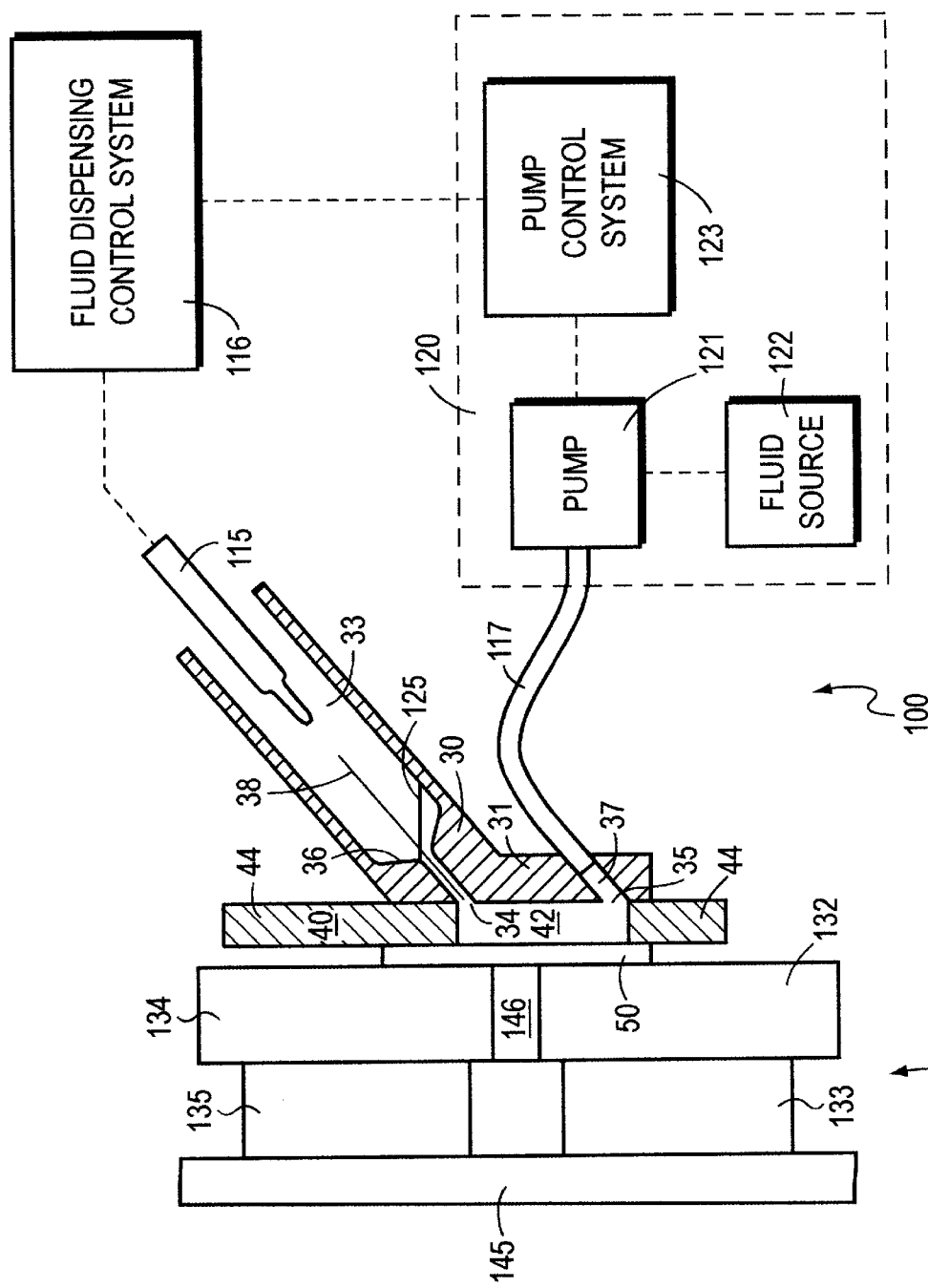
FIG. 2 schematically depicts a ferrograph incorporating the deposition cassette of FIG. 1

FIG. 2 shows the deposition cassette 20 of FIG. 1 as it is used with a ferrograph 100. The cassette 20 is mounted within a magnetic field established by a magnet structure 114. Ferrograph 100 has a fluid dispensing unit 115, such as an array of automatic pipettes controlled by a fluid dispensing control system 116, for directing a liquid into each of the reservoirs 33. The liquid from a reservoir eventually enters the respective flow chamber 42 and then exits through the respective outlet channel 37 and into respective outlet conduit 117. The outlet conduit 117 is in communication with a fluid transport system 120 for moving liquid from a fluid source into and out of the flow chamber 42. The fluid transport system 120 includes a pump 121 for each flow chamber 42, such as a syringe pump or a peristaltic pump, and may also include a source of priming fluid 122 and a pump control system 123. In a preferred embodiment, the fluid dispensing control system 116 is coupled to the fluid transport control system 123 to coordinate the delivery of liquid into the reservoirs 33 and its removal into the flow chambers 42 so that fluid remains at an appropriate level in the reservoirs 33 at all times. The fluid dispensing control system 116 and the fluid transport control system 123 preferably control the fluid dispensing unit 115 and the fluid transport system 120, respectively, to function independently with respect to each of the flow chambers 42.

The magnetic structure 114 has first and second magnetic pole members 132, 134 separated by an interpolar gap 146, and a magnetically permeable support member 145. Sandwiched between the pole members and support member 145 are first and second permanent magnets 133, 135. The interpolar gap 146 is, e.g., 1.25 mm wide along the length of a flow chamber 42 and 75 mm long across the five flow chambers 42. The pole members 132, 134 establish a magnetic flux density at the interpolar gap 146 that can range up to the saturation point of the pole pieces, generally on the order of 2 Tesla.

The deposition cassette 20 is disposed in the ferrograph 100 so that the elongated flow chamber 42 extends perpendicularly across the interpolar gap 146 approximately midway along the length of the chamber 42. The chamber 42 is disposed in a plane generally perpendicular to the opposed faces of pole members 132, 134, which define interpolar gap 146. The gap 146 is filled with a shim of a nonmagnetic material, such as aluminum, to keep the pole members separate and thus maintain the gap 146. In this instance, the deposition cassette 20 is mounted so that the flow chambers 42 extend in a vertical direction. The axis 38 of the reservoir forms a 45° angle with the vertical, so the included angle of the tapered section is less than 90° to promote drainage of fluid from the tapered section 36.

Dimensions in the deposition cassette 20 are selected for compatibility with the structure of the particular ferrograph 100, for enhancing the magnetically driven separation, and for imparting mechanical robustness to the cassette. For example, a ferrograph having a 0.050" magnet gap may use a five-chamber deposition cassette having a 0.005" sheet of borosilicate glass, about 1" wide in the flow direction and 2.5" long across the five chambers, functioning as substrate 50; a 0.02"-thick gasket 40 of silicone rubber, about 2" wide and 2.5" long; and a plastic platen with a planar portion about 1" wide and 2.75" long. If a thin glass sheet of the sort typically used as a cover slip for a microscope slide is used for the substrate, the used substrate and its deposits may be conveniently preserved and stored by mounting the used substrate on a heavier glass slide with the deposits between the substrate and the microscope slide. An inlet port is about 0.050" in diameter. Each chamber hole is about 0.25" wide and 0.625" long in the flow direction. The flared reservoirs 33 have a maximum inner diameter of approximately 0.25".

During operation of the ferrograph, for each flow chamber 42 the fluid transport system 120 directs priming fluid from the priming fluid source into the conduit 117, through outlet channel 37 and into the flow chamber 42. The priming fluid advances until it reaches some minimum level 125 in the reservoir at which bubbles will readily dissipate. The fluid dispensing control system 116 then activates the fluid dispensing unit 115 to add a first sample fluid containing suspended cells displaying magnetic properties to the reservoir 33 so as to form an interface between the priming fluid and the first sample fluid. The fluid transport control system 123 operates the pump 121 to draw the priming fluid, followed by the first sample fluid, back through the flow chamber 42. The liquid passes through the flow chamber 42 in a thin laminar layer (i.e., a layer having a laminar velocity profile). This strong magnetic field gradient adjacent the gap 146 of the magnet structure 114 draws the magnetically labeled cells toward a region of the substrate 50 overlying the gap 146.

Figure 3A:
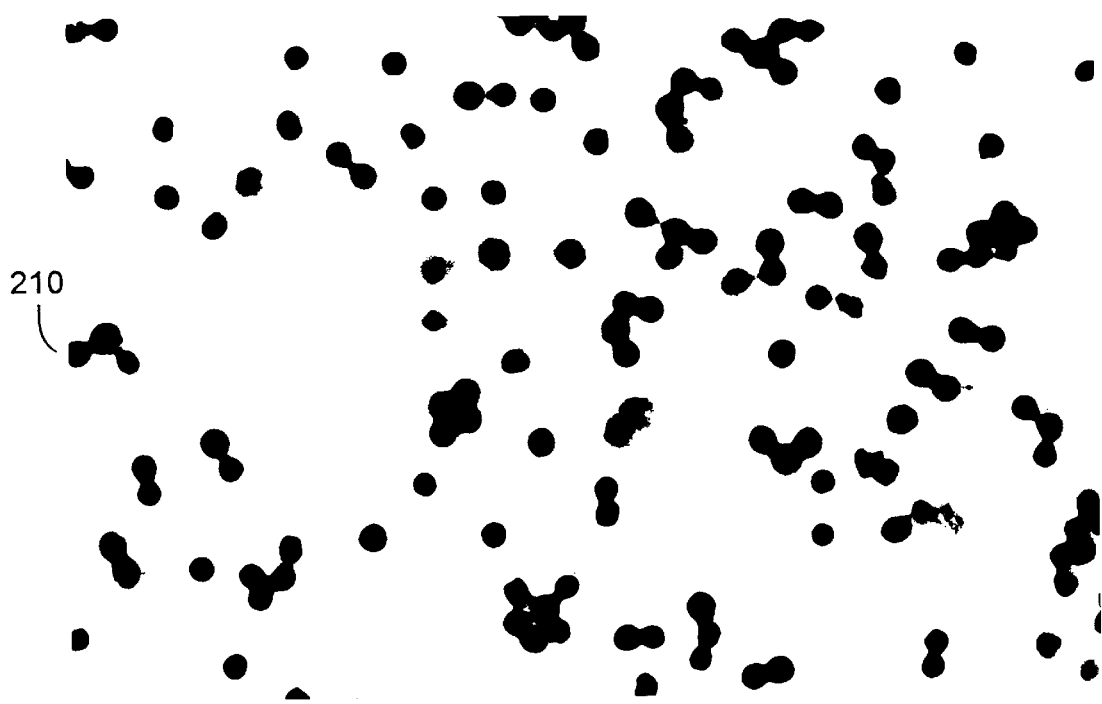
FIG. 3A is a photograph showing ferrographically deposited leukocytes stained and rinsed in situ using a high rinsing flow rate.
Figure 3B:
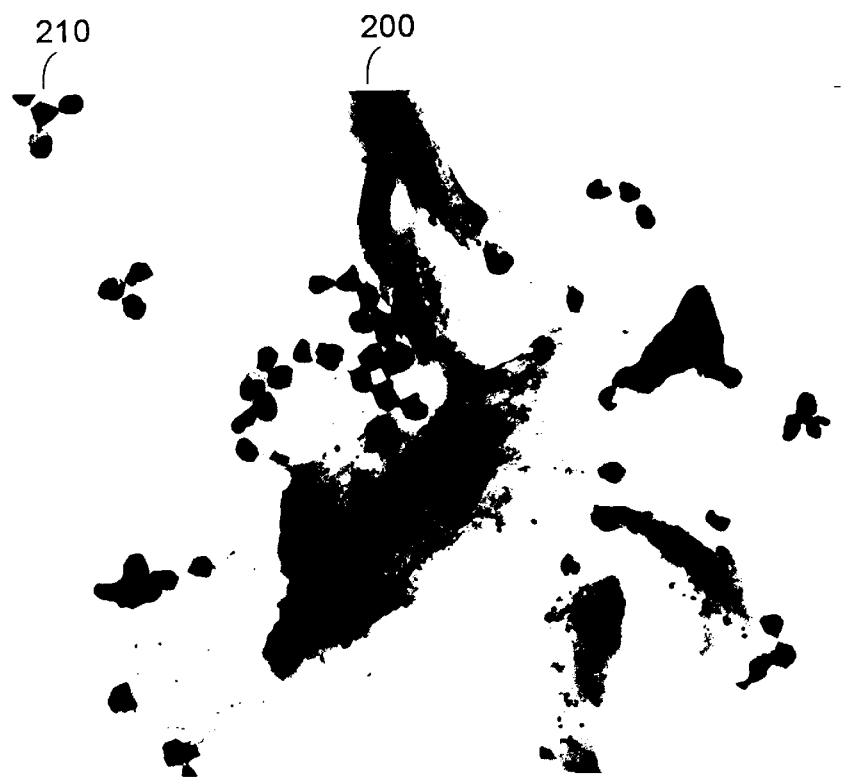
FIG. 3B is a photograph of ferrographically deposited leukocytes stained and rinsed by dipping the substrate respectively in staining and rinsing solutions.

If desired, the fluid dispensing unit 115 is then activated to add a second fluid, for example to rinse the deposit or impart a cytochemical staining agent, such as are well known to those skilled in the art, to the reservoir 33, while some first sample fluid remains at the minimum level 125. The fluid transport system 120 then draws the second fluid along the fluid pathway across the deposited cellular material on the substrate 50 and into the outlet conduit 117. A staining liquid may be followed in turn by a rinsing fluid. In a preferred embodiment, the fluid transport control system is configured to move fluid through the system at a slower rate during cell deposition, followed by a much faster rate for rinsing. As illustrated in FIG. 3A, applied after in situ staining, a rinsing rate much greater than the flow rate used during deposition affords very efficient removal of superfluous matter 200 originating in an alcohol-based stain from the deposited cells 210, especially in comparison with staining by dipping the slide in a staining solution followed by dipping in rinse solution, after disassembly of the deposition cassette 20, as shown by FIG. 3B.

Figure 4:
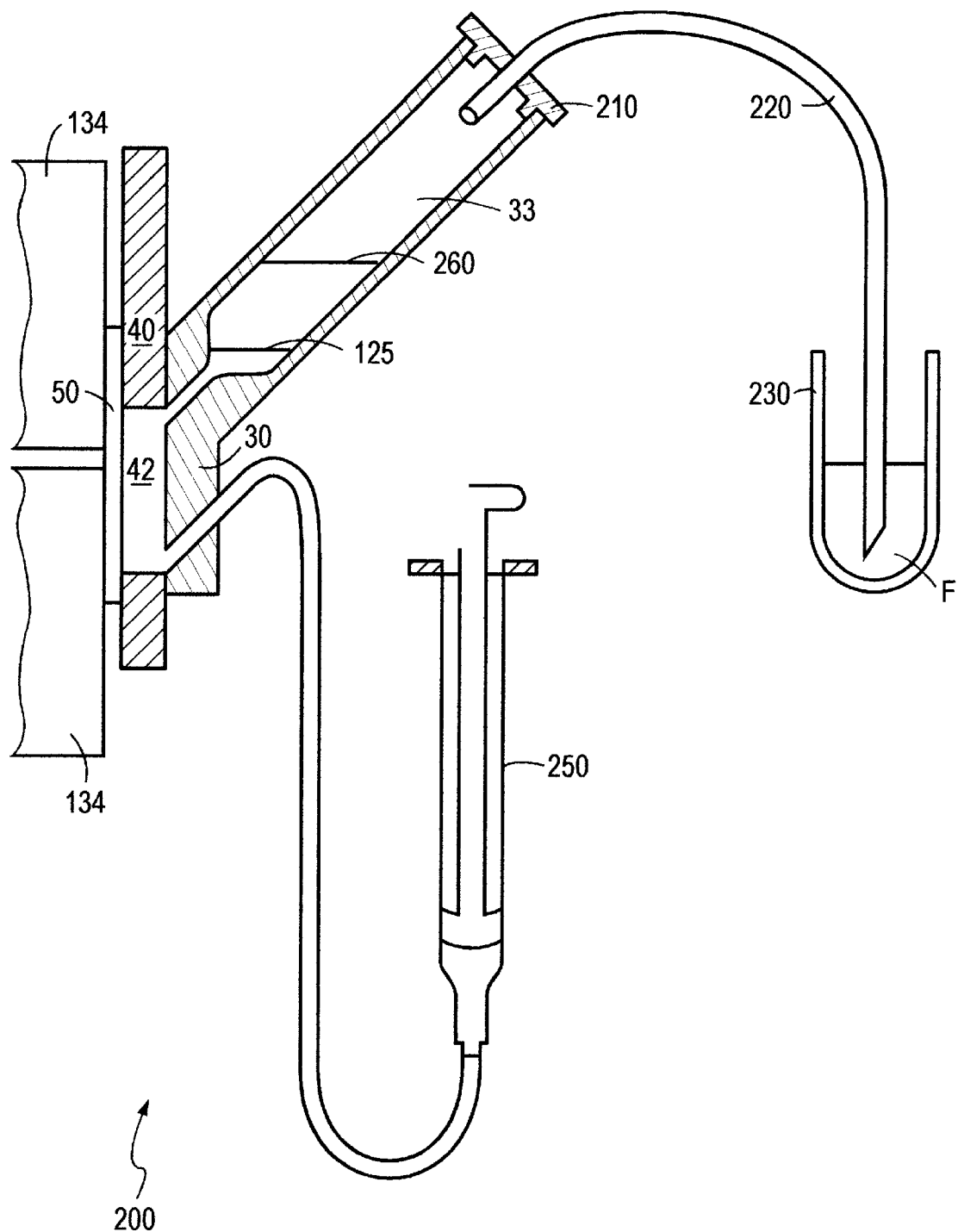
FIG. 4 schematically depicts a ferrograph in which the reservoir of the deposition cassette functions as a drip chamber.

FIG. 4 shows the deposition cassette 20 adapted for use with a ferrograph 200, in which each of the reservoirs 33 is sealed with an air-tight cap 210. The fluid dispensing system comprises a refill tube 220 having one end threaded through the cap 210 and extending into the reservoir 33 and the other end submerged under fluid in a bulk sample receptacle 230 vented to the atmosphere. The fluid transport system comprises a syringe 250. In operation, after priming, the reservoir 33 is filled with sample fluid above the minimum level 125 and then covered by cap 210. As the syringe 250 is operated to move sample fluid through the flow chamber, fluid F is drawn from the receptacle 230 into the reservoir 33 so as to keep the liquid level 260 in the reservoir 33 constant.

The labeled cells remaining on the substrate 50 form a characteristic "signature" band based on their relative magnetic susceptibilities. The deposition cassette 20 may then be removed from the magnetic structure 114. The cassette 20 may be disassembled to allow microscopic observation of the cells deposited on the substrate 50. Alternatively, the fluid delivery control system 116 and the fluid transport control system 123 may operate so as to direct a fluid into at least some of the flow chambers 42 in the cassette 20 in order to flush deposited cells into the outlet conduit 117 so that they may be collected and resuspended for further processing. Indeed, collected cells can be alive, and cultures grown therefrom.

A multi-chambered deposition cassette 20, with a gasket 40 having several chamber holes 42, is useful for performing simultaneous sorting of several portions of a bulk liquid. After assembly and loading into the ferrograph 100, each of the resulting flow chambers 42 has a respective deposition area disposed over the interpolar gap 146. The liquid is divided into separate aliquots, and a different cell subpopulation magnetically marked in each aliquot. Each aliquot is fed into a separate dispensing receptacle in the fluid dispensing system 115. Liquid is directed from each dispensing receptacle into a separate reservoir 33 in the platen 30. Such a multi-chambered flow unit can be used to particular advantage where ratios of different subpopulations are required, because simultaneous sorting of multiple cell types from the same sample avoids interference from extraneous experimental variables (e.g., temperature- and time-dependent concentration changes) that could influence results if the different cell types were sorted serially, one after another. This approach allows cells in one flow chamber of a multi-chambered cassette to be displaced out of the chamber by flushing after removing the cassette from the magnet, while the deposit in another chamber of the same cassette is left intact for microscopic observation. Alternatively, different dispensing receptacles can be used to hold separate, independent samples (i.e., from different sources), which can be processed concurrently by the ferrograph 100 simultaneously to save time.

It will therefore be seen that the foregoing represents a highly advantageous approach to ferrographic analysis, especially for use with biological materials. The possible uses of the invention set forth herein are but some that can be realized; others will be apparent to those skilled in the art. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of subjecting a first sample fluid to a magnetic field having a gradient penetrating a flow chamber, the method comprising the steps of:
   a. providing a deposition cassette comprising
      i. a substrate,
      ii. a gasket having at least one chamber hole therethrough, and
      iii. a platen having a respective inlet port and a respective outlet port, the gasket being interposed between and in contact with the substrate and the platen so as to form a liquid-tight seal around the at least one chamber hole, thereby forming a respective flow chamber in communication with the respective inlet and outlet ports;
   b. mounting the cassette in the gradient of the magnetic field so that the gradient penetrates the at least one flow chamber;

c. providing a respective reservoir in fluid communication with the respective inlet port;

d. advancing a priming fluid in a first direction through the respective outlet port into the at least one flow chamber and then out the respective inlet port into the respective reservoir so as to form a first meniscus in the respective reservoir;

e. adding the first sample fluid to the respective reservoir in contact with the first meniscus so as to form an interface between the priming fluid and the first sample fluid; and f. while the cassette is mounted in the gradient, moving first sample fluid from the respective reservoir in a second direction through the at least one flow chamber and then out the respective outlet port so as to displace the priming fluid from the at least one flow chamber, the second direction being opposite to the first direction.

2. The method of claim 1 wherein the at least one chamber hole comprises a plurality of chamber holes, the deposition cassette having a plurality of flow chambers, each flow chamber having a respective inlet port, outlet port and reservoir.

3. The method of claim 1 wherein the movement of fluid through one of the plurality of flow chambers is controlled independently of the movement of fluid through another one of the plurality of flow chambers.

4. The method of claim 1 wherein the interface between the priming fluid and the first sample fluid remains intact during steps e. and f.

5. The method of claim 1 wherein steps d. and f. are performed by a pump in communication with the respective outlet port, step c. comprising driving priming fluid in the first direction away from the pump, step e. comprising drawing first sample fluid in a second direction toward the pump.

6. The method of claim 1 wherein the respective reservoir has a tapered section over which a diameter of the reservoir increases from its value at the inlet port to a value sufficiently large to allow ready dissipation of a gas bubble.

7. The method of claim 1 wherein the respective reservoir is integral to the platen.

8. The method of claim 1 wherein the first sample fluid contains material displaying magnetic properties.

9. The method of claim 8 wherein the material displaying magnetic properties interacts with the penetrating gradient of the magnetic field so as to cause the material to deposit onto the substrate.

10. The method of claim 9 wherein the material displaying magnetic properties is a biological material that has been magnetized.

11. The method of claim 9 further comprising a flushing operation including the steps of:

a. adding a flushing fluid to the respective reservoir, thereby forming in the reservoir an interface between the flushing fluid and a liquid filling the flow chamber;

b. moving the deposition cassette so that the gradient of the magnetic field no longer penetrates the at least one flow chamber;

c. drawing flushing fluid from the respective reservoir in the second direction through the at least one flow chamber and out the respective outlet port so as to remove deposited material displaying magnetic properties from the substrate and convey it out the outlet port.

12. The method of claim 11 wherein a sample fluid moves through the at least one flow chamber at a sample rate and the flushing fluid moves through the flow chamber during step at a flushing rate equal to at least 50 times the sample rate.

13. The method of claim 11 wherein a sample fluid moves through the at least one flow chamber at a sample rate and the flushing fluid moves through the flow chamber during steps at a flushing rate greater than the sample rate.

14. The method of claim 1 wherein first sample fluid moves in the second direction through the at least one flow chamber during step e. at a first sample rate and priming fluid moves in the first direction through the at least one flow chamber during step c. at a priming rate equal to at least 10 times the first sample rate.

15. The method of claim 1 wherein no gas bubbles are present in the at least one flow chamber, the respective inlet port or reservoir after step c.

16. The method of claim 1 wherein the first sample fluid forms a second meniscus in the reservoir and further comprising the steps of:

a. adding a second fluid to the respective reservoir in contact with the second meniscus, thereby forming an interface between the first sample fluid and the second fluid; and b. drawing second fluid from the respective reservoir in the second direction through the at least one flow chamber and out the respective outlet port by negative pressure so as to displace the first sample fluid from the at least one flow chamber.

17. The method of claim 16 wherein the interface between the first and second fluids remains substantially intact during steps a. and b.

18. The method of claim 16 wherein the first sample fluid contains material displaying magnetic properties that interacts with the penetrating gradient of the magnetic field so as to cause the material to deposit onto the substrate, the second fluid containing a substance for reacting with deposited material.

19. The method of claim 18 wherein the second fluid is a staining solution.

20. The method of claim 16 wherein the first sample fluid contains material displaying magnetic properties that interacts with the penetrating gradient of the magnetic field so as to cause the material to deposit onto the substrate, the second fluid effecting removal of extraneous deposited matter.

21. The method of claim 20 wherein a sample fluid moves through the at least one flow chamber at a sample rate and the second fluid moves through the flow chamber while being drawn through the at least one flow chamber at a rinsing rate equal to at least 20 times the sample rate.

22. The method of claim 1 wherein first sample fluid moves in the second direction through the at least one flow chamber during step e. at a first sample rate and priming fluid moves in the first direction through the at least one flow chamber during step c. at a priming rate greater than the first sample rate.

* * * * *